US00PP15002P2

(12) United States Plant Patent
Strope

(10) Patent No.: US PP15,002 P2
(45) Date of Patent: Jul. 13, 2004

(54) PETUNIA PLANT NAMED 'BALRUFIMPU'

(50) Latin Name: *Petunia×hybrida*
Varietal Denomination: Balrufimpu

(75) Inventor: Kerry M. Strope, Pismo Beach, CA (US)

(73) Assignee: Ball Floraplant, a division of Ball Horticultural Co., West Chicago, IL (US)

( * ) Notice: Subject to any disclaimer, the term of this patent is extended or adjusted under 35 U.S.C. 154(b) by 81 days.

(21) Appl. No.: 10/107,712

(22) Filed: Mar. 26, 2002

(51) Int. Cl.[7] ..... A21H 5/00
(52) U.S. Cl. ..... Plt./356
(58) Field of Search ..... Plt./356

*Primary Examiner*—Bruce R. Campell
*Assistant Examiner*—Michelle Kizilkaya
(74) *Attorney, Agent, or Firm*—Wood, Phillips, Katz, Clark & Mortimer

(57) ABSTRACT

A new and distinct Petunia plant named 'Balrufimpu', characterized by its double purple flowers, mounded-trailing habit and dark green leaves.

2 Drawing Sheets

Latin name of the genus and species of plant claimed: *Petunia×hybrida*
Variety denomination: 'Balrufimpu'

BACKGROUND OF THE INVENTION

The present invention comprises a new and distinct Double Petunia plant, botanically known as *Petunia×hybrida*, and hereinafter referred to by the cultivar name 'Balrufimpu'.

'Balrufimpu' is the result of a planned breeding program with the objective of developing Petunia cultivars with large, fully double flowers and vigorous mounded-trailing growth habits.

The female parent of 'Balrufimpu' was the proprietary *Petunia×hybrida* variety, designated 'BFP-200' (not patented), which exhibits an upright habit and double white flowers. The male parent of 'Balrufimpu' was the proprietary *Petunia×hybrida* variety, designated '3399-3' (not patented), which exhibits a trailing habit and single purple flowers. The new cultivar was discovered and selected as a single seedling originating from within the progeny of the above stated cross during September 1998 in a controlled environment at Arroyo Grande, Calif. and was initially designated 'BFP-710'.

Asexual reproduction of the new cultivar has been carried out at Arroyo Grande, Calif. and West Chicago, Ill. by terminal tip cuttings and has demonstrated that the unique characteristics of the new cultivar as herein described are firmly fixed and retained through successive generations of such asexual propagation.

SUMMARY OF THE INVENTION

It was found that the cultivar of the present invention:

(a) exhibits double purple flowers;

(b) forms dark green foliage;

(c) exhibits a good basal branching character; and (d) exhibits a vigorous mounded-trailing growth habit.

The new cultivar of the present invention can be compared to Marco Polo™ Adventurer (patent status and denomination unknown by the inventor). In side-by-side comparisons, plants of the new cultivar are more vigorous, have small flowers than March Polo™ Adventurer.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 12 weeks in a greenhouse at West Chicago, Ill., U.S.A.

DETAILED BOTANICAL DESCRIPTION

The cultivar 'Balrufimpu' has not been observed under all possible environmental conditions to date. Accordingly, it is possible that the phenotype may vary somewhat with variations in the environment, such as temperature, light intensity, and day length. The chart used in the identification of colors described herein is the R.H.S. Colour Chart of The Royal Horticultural Society, London, England. The color values were determined on Oct. 15, 2001. The readings were taken between 1:00 and 3:00 p.m. under natural daylight conditions.

Plants used for the following descriptions and measurements were grown 10 cm pots for 12 weeks from rooted cuttings. The plants were produced from cuttings taken from stock plants and grown in double poly carbonate covered greenhouse under conditions comparable to those used in commercial practice. A soilless growth medium was utilized while temperatures of approximately 55° to 75° F. (13° to 24° C.) during the day and approximately 50° to 60° F. (10° to 16° C.) during the night and light levels of 5,000 to 8,000 footcandles were maintained.

Classification:
*Botanical.*—*Petunia×hybrida* cultivar 'Balrufimpu'.
Parentage:
*Female parent.*—Proprietary *Petunia×hybrida* variety designated 'BFP-200'.
*Male parent.*—Proprietary *Petunia×hybrida* variety designated '3399-3'.
Propagation:
*Type cutting.*—Terminal tip.

*Time to initiate roots.*—Approximately 7 to 10 days.

*Time to develop roots.*—Approximately 21 to 30 days.

*Root description.*—Fibrous, branching.

Plant Description:

*Crop time.*—Approximately 6 to 8 weeks are required to produce a finished plant from rooted cuttings.

*Habit of growth.*—Vigorous with good basal branching. Pinching improves basal branching.

*Form.*—Mount-trailing.

*Plant height.*—A mature plant, 12 weeks after the planting of a rooted cutting, commonly measures approximately 13.2 from the soilline to the top of the plant plane.

*Plant spread.*—Approximately 45 cm.

*Lateral branches.*—An average of 5 branches per plant, approximately 28 cm in length and 3 mm in diameter, densely pubescent and 144A in color. Internode length at the middle of the branch is approximately 3.3 cm.

*Foliage.*—Leaves are non-fragrant, single and the arrangement is alternate along the stem becoming opposite at the base of the peduncle. Leaves are ovate with entire margin, broadly acute apex, attenuate base and are at an acute angle to the stem. Upper and lower surfaces are densely pubescent and the margin is densely pubescent. There are approximately 15 leaves per branch. Leaf length is approximately 3.2 cm and width is approximately 2.2 cm. The upper surface of young foliage is lighter and more yellow than 147A and the lower surface is 147B. The upper surface of mature foliage is 147A and the lower surface is closest to 147B. Both upper and lower surfaces have pinnate venation closest to 144A. The petiole length is approximately 7 mm, the diameter is approximately 3 mm and the color is closest to 144C.

Flowering Description:

*Flowering habit.*—Freely flowering.

*Natural flowering season.*—Year round in greenhouse environment and from spring through fall in outdoor garden

*Lastingness of the bloom.*—The bloom remains approximately 5–7 days.

Flower Description:

*Type.*—Double, solitary, axillary, salverform, with pungent fragrance. Flowers are persistent.

*Size.*—Length (height) is approximately 4.2 cm and width is approximately 5.3 cm.

*Corolla.*—Approximately 10 obovate petals with the outer whorl of five petals fused to form corolla tube. All petals have rounded apex, entire undulate margin and smooth texture. Petal length from throat is 2 cm and width at widest point is 2.4 cm. Color of upper surface is closest to 67A with midvein of 79A. Color of lower surface is 67C with midvein of 144C.

*Corolla tube.*—Length is approximately 2.6 cm, diameter at distal end is approximately 5 mm and diameter at proximal end is approximately 1.4 cm. Color of outer surface is 145D with venation of 144C. Color of inner surface is 77B at rim with the rest of the length being 144D, with venation of 79A. The outer surface is moderately pubescent and inner surface is smooth.

*Peduncle.*—Densely pubescent, at an acute angle to the stem, approximately 1.5 cm in length and 1 mm in diameter. Peduncle color is 144A.

*Flower bud.*—Ovate, elongating as it matures, approximately 3.5 cm in length and 1 cm in diameter at first color. Color is 83A.

*Sepals.*—Five, non-imbricate, approximately 1.4 cm in length, 3 mm in diameter, linear in shape and broadly acute apex and entire, slightly undulate margin. Both surfaces are densely pubescent. The color of the upper surface is 144A and the lower surface is 146B.

*Reproductive organs.*—Stamen number is approximately 8. Anther shape is oval and length is approximately 2 mm. Pollen is moderate and color is grayer than 106D. The single pistil is approximately 1.9 cm in length. Stigma is funnel shape, 143B. Style is 1.3 cm in length and color is 144D. Ovary size is approximately 3 mm and the color is 143C.

Seed production: Seed production has not been observed.

Disease resistance: Resistance to pathogens has not been observed.

I claim:

1. A new and distinct cultivar of Petunia plant named 'Balrufimpu' substantially as herein shown and described, which:

(a) exhibits double purple flowers;

(b) dark green foliage;

(c) a good basal branching character; and (d) a mounded-trailing growth habit.

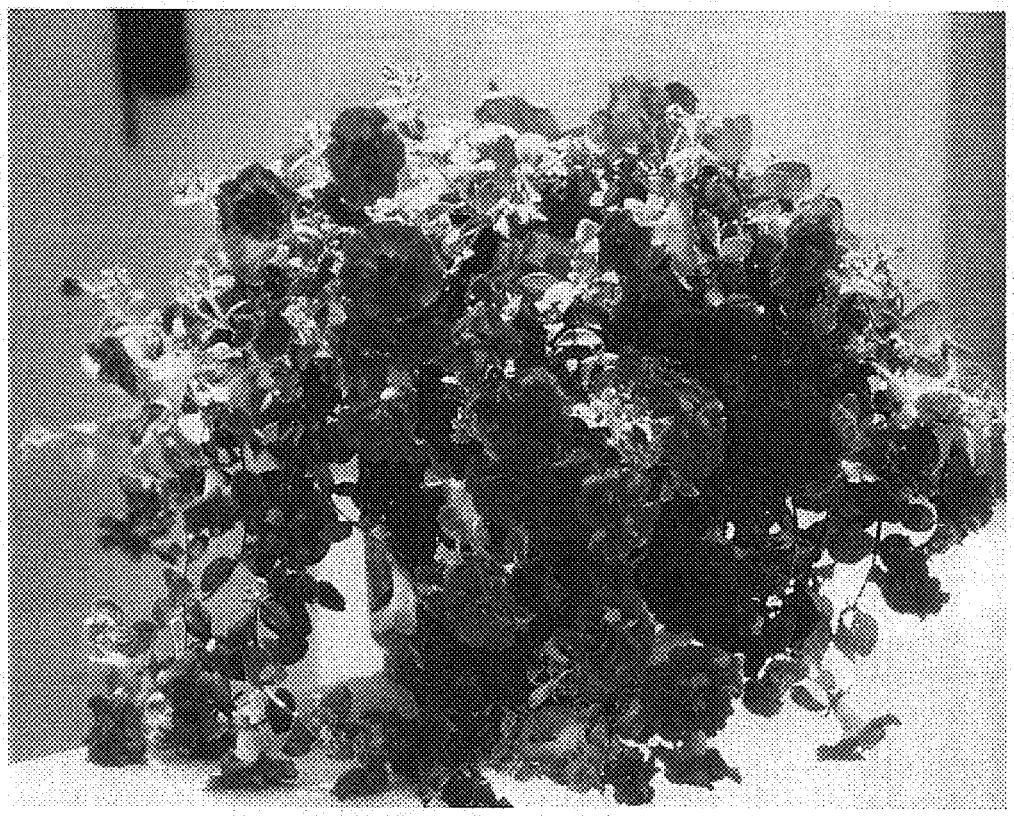

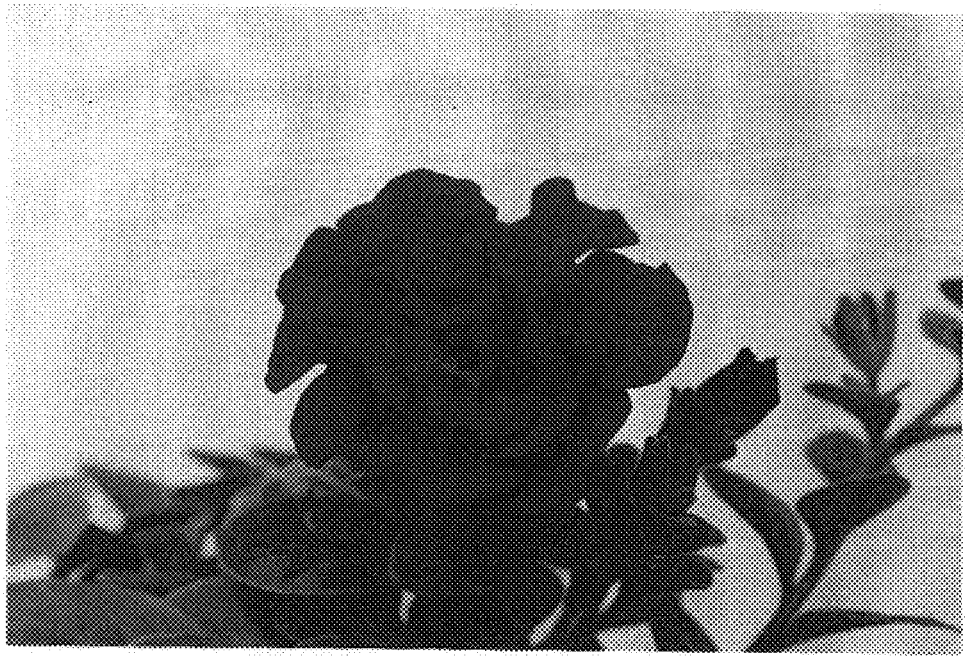

* * * * *